United States Patent
Shimizu et al.

(10) Patent No.: US 8,927,016 B2
(45) Date of Patent: Jan. 6, 2015

(54) PRODUCING A SUSTAINED-RELEASE PREPARATION

(75) Inventors: Hisayoshi Shimizu, Takatsuki (JP); Muneo Nonomura, Toyonaka (JP); Tomomichi Futo, Osaka (JP); Kei Mukai, Katano (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/926,520

(22) Filed: Nov. 23, 2010

(65) Prior Publication Data

US 2011/0070311 A1  Mar. 24, 2011

Related U.S. Application Data

(60) Continuation of application No. 11/001,889, filed on Dec. 2, 2004, now abandoned, which is a division of application No. 09/600,744, filed as application No. PCT/JP99/00175 on Jan. 20, 1999, now abandoned.

(30) Foreign Application Priority Data

Jan. 21, 1998 (JP) ................... 10-009911

(51) Int. Cl.
*A61K 9/26* (2006.01)
*A61K 9/14* (2006.01)
*A61K 9/16* (2006.01)
*A61K 38/09* (2006.01)
*F26B 5/06* (2006.01)
*A61K 9/19* (2006.01)

(52) U.S. Cl.
CPC ................. *A61K 9/1647* (2013.01); *F26B 5/06* (2013.01); *A61K 9/19* (2013.01)
USPC ........... 424/469; 424/484; 424/491; 514/10.4

(58) Field of Classification Search
None
See application file for complete search history.

(56) References Cited

U.S. PATENT DOCUMENTS

| | | | |
|---|---|---|---|
| 3,928,566 A | * | 12/1975 | Briggs et al. ................. 424/94.3 |
| 4,722,943 A | | 2/1988 | Melber et al. |
| 4,878,597 A | | 11/1989 | Haast |
| 5,044,091 A | | 9/1991 | Ueda et al. |
| 5,514,670 A | | 5/1996 | Friedman et al. |
| 5,534,269 A | | 7/1996 | Igari et al. |
| 5,594,091 A | | 1/1997 | Igari et al. |
| 5,665,428 A | | 9/1997 | Cha et al. |
| 5,888,531 A | | 3/1999 | Ohshika et al. |
| 6,117,455 A | | 9/2000 | Takada et al. |
| 6,190,700 B1 | | 2/2001 | Okada et al. |
| 2001/0006678 A1 | | 7/2001 | Takada et al. |
| 2001/0014339 A1 | | 8/2001 | Shigeyuki et al. |
| 2001/0018075 A1 | | 8/2001 | Shigeyuki et al. |
| 2002/0050072 A1 | | 5/2002 | Akimoto et al. |
| 2002/0189127 A1 | | 12/2002 | Akimoto et al. |

FOREIGN PATENT DOCUMENTS

| | | |
|---|---|---|
| CA | 2235602 | 5/1997 |
| EP | 0 145 240 | 6/1985 |
| EP | 0 190 833 | 8/1986 |
| EP | 0 394 050 | 10/1990 |
| EP | 0 442 671 | 2/1991 |
| EP | 0 442 071 | 8/1991 |
| EP | 0 535 937 | 4/1993 |
| EP | 0 582 459 | 2/1994 |
| EP | 0 586 238 | 3/1994 |
| EP | 0 761 213 | 3/1997 |
| EP | 0 781 548 | 7/1997 |
| JP | 63-049683 A | 3/1988 |
| JP | 05-003904 A | 1/1993 |
| JP | 08-151321 A | 6/1996 |
| JP | 08-208706 A | 8/1996 |
| JP | 09-095440 A | 4/1997 |
| JP | 09-221417 A | 8/1997 |
| WO | WO 89/04673 | 6/1989 |

OTHER PUBLICATIONS

Office Action mailed Jun. 9, 2009, in corresponding JP 11-011495, 3 pages, with English translation, 4 pages.
Adams et al., "Freeze-drying of biological materials," Drying Technology, 1991, 9(4):891-924.

* cited by examiner

*Primary Examiner* — Jeffrey T Palenik
(74) *Attorney, Agent, or Firm* — Foley & Lardner LLP

(57) ABSTRACT

This invention provides a production method for a solid sustained-release preparation, characterized in that a sustained-release preparation (a sustained-release preparation suspension) is freeze-dried in a freeze-drying container whose inner face is partially or totally coated with an ice layer or water-repelling base material.

9 Claims, No Drawings

PRODUCING A SUSTAINED-RELEASE PREPARATION

CROSS-REFERENCE TO RELATED APPLICATIONS

This application is a Continuation of U.S. Ser. No. 11/001,889, filed Dec. 2, 2004, which is a Divisional of U.S. Ser. No. 09/600,744, which is the US National Stage of PCT/JP1999/00175, filed Jan. 20, 1999, which claims priority from Japanese application JP 10-009911, filed Jan. 21, 1998.

TECHNICAL FIELD

The present invention relates to a production method for a solid sustained-release preparation such as in a microsphere form that enables easy recovery of the solid sustained-release preparation without extended environmental exposure.

BACKGROUND ART

A microcapsure (microsphere) (hereinafter also referred to as MC) is first prepared by the aqueous drying method, etc., then separated, concentrated and recovered, after which mannitol etc. are added and dissolved, to yield an MC suspension, which is then dehydrated and dried by freeze-drying to yield a finished microcapsule powder (microsphere powder) (hereinafter also referred to as MC powder). In this operation, it is common practice to dispense the MC suspension to a tray and freeze-dry the suspension.

However, because of the necessity of manual aseptic removal and recovery of the MC powder from the tray using a scraper after completion of freeze-drying, the conventional method has the drawbacks described below.

(1) MC powder adhesion to the tray necessitates the removal of MC powder using a scraper at the time of its recovery.
(2) Because scraping is conducted manually, and because it takes a relatively long time to recover the MC, the MC is exposed to the environment for an extended period of time, resulting in the constant risk of contamination with microorganisms etc., an aspect undesirable from the viewpoint of assurance of sterility. Also, because the MC preparations need water content control, such long environmental exposure poses a risk from the viewpoint of physicochemical stability.
(3) Because the use of a scraper is essential for the scraping process, there is a risk of production and invasion of foreign substances attributable to friction between the tray and scraper.
(4) Because of adhesion of the MC powder and tray, some MC powders ramin on the tray and unrecovered, even after scraping.

DISCLOSURE OF INVENTION

Against this background there has been a demand for the development of a production method for a solid sustained-release preparation that enables easy recovery of the solid sustained-release preparation after freeze-drying at high recovery rates, with short environmental exposure time and reduced risk for production and introduction of foreign substances.

After extensive investigation aiming at resolving the above problem, the present inventors have found that by previously forming an ice layer or coating the inner face of the tray with a water-repelling base material, the freeze-dried MC powder can unexpectedly be recovered in a short time and with ease. Further, the present inventors have found that by completing the sublimation of frozen water in the freeze-drying container under reduced condition that the temperature in the freeze-drying container is 0° C. or below, the freeze-dried cake does not collapse or scatter, and consequently, the freeze-dried MC powder can be recovered unexpectedtly in a good form and high yield. The inventors have conducted further investigation based on this finding, and developed the present invention.

Accordingly, the present invention provides:
(1) a method for producing a solid sustained-release preparation, which comprises freeze-drying a sustained-release preparation in a freeze-drying container of which the inner face is partially or wholly coated with an ice layer or water-repelling base material,
(2) a method for producing a solid sustained-release preparation, which comprises freeze-drying a sustained-release preparation in a freeze-drying container of which the inner face is partially or wholly coated with a water-repelling base material, and the coated inner face is further partially or wholly coated with an ice layer,
(3) the method according to term (1) or (2) above wherein the inner face is the bottom face alone,
(4) the method according to term (1) or (2) above wherein the freeze-drying container is a tray,
(5) the method according to term (1) or (2) above wherein the ice layer has a thickness of about 0.01 mm to about 30 mm,
(6) the method according to term (1) or (2) above wherein the water-repelling base material is ethylene tetrafluoride resin, ethylene trifluoride resin, ethylene difluoride resin, vinylidene fluoride resin, propylene hexafluoride-ethylene tetrafluoride copolymer resin, modified fluorine resin, ethylene tetrafluoride-perfluoroalkoxyethylene copolymer resin, or ethylene tetrafluoride-ethylene copolymer resin,
(7) the method according to any one of terms (1) through (6) above wherein said sustained-release preparation is a microsphere, and
(8) the method according to term (1) or (2) above which comprises completing the sublimation of frozen water in the freeze-drying container under reduced condition that the temperature in the freeze-drying container is 0° C. or below, The present invention further provides:
(9) the production method according to term (1) or (2) above wherein the thickness of said ice layer is about $\frac{1}{1,000}$ to about $\frac{4}{5}$ of the depth of the container,
(10) the production method according to term (1) or (2) above wherein the thickness of the frozen layer of the sustained-release preparation suspension is $\frac{1}{1,000}$ to about $\frac{4}{5}$ of the depth of the container,
(11) the production method according to term (1) or (2) above wherein the size of the container is about 5 mm to about 7,000 mm in width, about 5 mm to about 7,000 mm in length, and about 1 mm to 100 mm in depth, and wherein the ice layer is about 0.01 mm to about 30 mm,
(12) the production method according to any one of terms (1) through (11) above wherein said sustained-release preparation is a sustained-release preparation containing a biologically active peptide,
(13) the production method according to any one of terms (1) through (11) above wherein said sustained-release preparation is a sustained-release preparation containing a biologically active peptide and a biodegradable polymer,
(14) the production method according to term (12) or (13) above wherein said biologically active peptide is an LH-RH agonist or LH-RH antagonist, (15) the production method according to term (12) or (13) above wherein said biologically active peptide is 5-oxo-Pro-His-Trp-Ser-Tyr-DLeu-Leu-Arg-Pro-NH—$C_2H_5$ (leuprorelin) or a salt thereof,

(16) the production method according to term (12) or (13) above wherein said biologically active peptide is the acetate of 5-oxo-Pro-His-Trp-Ser-Tyr-DLeu-Leu-Arg-Pro-NH—$C_2H_5$ (leuprorelin),

(17) the production method according to term (13) above wherein said biodegradable polymer is an α-hydroxycarboxylic acid, polymer,

(18) the production method according to term (17) above wherein said α-hydroxycarboxylic acid polymer is a lactic acid-glycolic acid polymer,

(19) the production method according to term (18) above wherein the content ratio of lactic acid and glycolic acid is about 100/0 to about 40/60 (mol %),

(20) the production method according to term (18) above wherein the weight-average molecular weight of the polymer is about 3,000 to about 100,000,

(21) the production method according to term (13) above wherein said biodegradable polymer is polylactic acid, and

(22) the production method according to term (21) above wherein the weight-average molecular weight of the polylactic acid is about 10,000 to about 60,000.

Sustained-release preparations for the production method of the present invention include, for example, microspheres. The term "microsphere", as used herein, is understood to include microcapsules and microparticles.

Specifically, there may be used the microspheres, microcapsules, or the like, described in Japanese Patent Unexamined Publication Nos. 100516/1985, 201816/1987, 124814/1990, 321622/1992, 112468/1993, 194200/1993, 293636/1994, 145046/1994, 192068/1994, 169818/1996, 132524/1997, 221417/1997 and 221418/1997, and elsewhere.

The drug contained in the above-described sustained-release preparation is preferably a biologically active peptide, exemplified by biologically active peptides having molecular weights of about 300 to about 40,000, preferably about 400 to about 30,000, and more preferably about 500 to about 20,000.

Preferably, such biologically active peptides have a basic group capable of forming a salt with a weak acid having a pKa value of not less than 4.0 (e.g., carbonic acid, bicarbonic acid, boric acid, lower alkane-monocarboxylic acids having 1 to 3 carbon atoms). Said biologically active peptide may have an acidic group, whether free or salt form, in addition to a basic group.

A representative activity of said biologically active peptides is hormone action. Said biologically active peptide may be a naturally occurring substance, synthetic substance, semi-synthetic substance, or genetic engineering product, and may also be an analog and/or derivative thereof. The mechanism of action of these biologically active peptides may be agonistic or antagonistic.

Said biologically active peptide is exemplified by luteinizing hormone-releasing hormone (also referred to as LH-RH or gonadotropin-releasing hormone, Gn-RH), insulin, somatostatin, somatostatin derivatives (e.g., Sandostatin; U.S. Pat. Nos. 4,087,390, 4,093,574, 4,100,117 and U.S. Pat. No. 4,253,998), growth hormone (GH), growth hormone-releasing hormone (GH-RH), prolactin, erythropoietin (EPO), adrenocorticotropic hormone (ACTH), ACTH derivatives (e.g., ebiratide), melanocyte-stimulating hormone (MSH), thyroid hormone-releasing hormone ((pyr)Glu-His-ProNH$_2$; TRH), salts and derivatives thereof (Japanese Patent Unexamined Publication Nos. 121273/1975 and 116465/1977), thyroid-stimulating hormone (TSH), luteinizing hormone (LH), follicle-stimulating hormone (FSH), vasopressin, vasopressin derivatives (e.g., desmopressin), oxytocin, calcitonin, glucagon, gastrin, secretin, pancreozymin, cholecystokinin, angiotensin, human placental lactogen, human chorionic gonadotropin (HCG), enkephalin, enkephalin derivatives (e.g., U.S. Pat. No. 4,277,394, EP-31567), endorphin, kyotorphin, interferons (e.g., interferon-α, -β, -γ), interleukins (e.g., interleukins 1 through 12), tuftsin, thymopoietin, thymosin, thymostimulin, thymic humoral factor (THF), blood thymic factor (FTS) and derivatives thereof (U.S. Pat. No. 4,229,438), tumor necrosis factor (TNF), colony-stimulating factors (e.g., CSF, GCSF, GMCSF, MCSF), motilin, dynorphin, bombesin, neurotensin, caerulein, bradykinin, atrial natriuresis-increasing factor, nerve growth factor (NGF), cell growth factors (e.g., EGF, TGF-β, PDGF, acidic FGF, basic FGF), neurotrophic factors (e.g., NT-3, NT-4, CNTF, GDNF, BDNF), endothelin-antagonistic peptides and analogs (derivatives) thereof (EP-436189, EP-457195, EP-496452, Japanese Patent Unexamined Publication Nos. 94692/1991 and 130299/1991), insulin receptors, insulin-like growth factor (IGF)-1 receptor, IGF-2 receptor, transferrin receptor, epidermal growth factor, low-density lipoprotein (LDL) receptor, macrophage scavenger receptor, GLUT-4-transporter, growth hormone receptor, leptin receptor internalization-inhibiting MHC-I (major histocompatibility class I antigen complex) α1 domain-derived peptide (Proceedings of the National Academy of Sciences of the United States of America, Vol. 91, pp. 9086-9090 (1994); ibid., Vol. 94, pp. 11692-11697 (1997)) and analogs (derivatives) thereof, and fragments thereof and fragment derivatives thereof.

When the biologically active peptide is a salt, the salt is exemplified by pharmacologically acceptable salts. For example, when said biologically active peptide has a basic group such as an amino group in the molecular structure thereof, such salts include salts of said basic group and inorganic acids (e.g., hydrochloric acid, sulfuric acid, nitric acid, boric acid), organic acids (e.g., carbonic acid, bicarbonic acid, succinic acid, acetic acid, propionic acid, trifluoroacetic acid) etc. When said biologically active peptide has an acidic group such as a carboxyl group in the molecular structure thereof, such salts include salts with inorganic base materials (e.g., alkali metals such as sodium and potassium, alkaline earth metals such as calcium and magnesium), organic base materials (e.g., organic amines such as triethylamine, basic amino acids such as arginine) etc. The biologically active peptide may form a metal complex compound (e.g., copper complex, zinc complex).

Preferred examples of the biologically active peptide for the present invention include LH-RH analogs or salts thereof that are effective against diseases dependent on LH-RH or hormones derived therefrom, such as prostatic cancer, prostatic hypertrophy, endometriosis, hysteromyoma, metrofibroma, precocious puberty and breast cancer, and effective for contraception, and somatostatin derivatives and salts thereof that are effective against diseases dependent on growth hormone or hormones derived therefrom, and gastrointestinal diseases such as digestive ulcer.

Examples of such LH-RH analogs include, for example, the peptides described in "Treatment with GnRH Analogs: Controversies and Perspectives" (The Parthenon Publishing Group Ltd., published 1996), Japanese Patent Examined Publication No. 503165/1991, Japanese Patent Unexamined Publication Nos. 101695/1991, 97334/1995 and 259460/1996, and elsewhere.

Biologically active peptides possessing LH-RH antagonistic action (LH-RH antagonists) include, for example, biologically active peptides represented by general formula [Ia]:

X-D2Nal-D4ClPhe-D3Pal-Ser-A-B-Leu-C-Pro-DAlaNH$_2$

[X represents N(4H$_2$-furoyl)Gly or NAc; A represents a residue selected from NMeTyr, Tyr, Aph(Atz) and NMeAph (Atz); B represents a residue selected from DLys(Nic), DCit, DLys(AzaglyNic), DLys(AzaglyFur), DhArg(Et$_2$), DAph (Atz) and DhCi; C represents Lys(Nisp), Arg or hArg(Et$_2$)] or salts thereof. These peptides can be produced by the methods described in the above-mentioned references or patent publications, or methods based thereon.

Biologically active peptides possessing LH-RH agonistic action (LH-RH agonists) include, for example, biologically active peptides represented by general formula [Ib]:

5-oxo-Pro-His-Trp-Ser-Tyr-Y-Leu-Arg-Pro-Z

[Y represents a residue selected from DLeu, DAla, DTrp, DSer(tBu), D2Nal and DHis(ImBzl); Z represents NH—C$_2$H$_5$ or Gly-NH$_2$] or salts thereof. Peptides wherein Y is DLeu and Z is NH—C$_2$H$_5$, in particular, are preferred. These peptides can be produced by the methods described in the above-mentioned references or patent publications, or methods based thereon.

Examples of somatostatin derivatives or salts thereof are described in, for example, the Proceedings of the National Academy of Sciences of the United States of America, Vol. 93, pp. 12513-12518 (1996), and the references cited therein.

Of the somatostatin derivatives, those that are selectively effective against tumors include, for example, the biologically active peptides described in the patent publications for U.S. Pat. No. 5,480,870 and EP-05056800, and salts thereof, such as DPhe-Cys-Tyr-DTrp-Lys-Cys-ThrNH$_2$.

Sandostatin (U.S. Pat. Nos. 4,087,390, 4,093,574, 4,100,117, 4,253,998) etc. are also preferred.

Of the above-mentioned biologically active peptides, 5-oxo-Pro-His-Trp-Ser-Tyr-DLeu-Leu-Arg-Pro-NH—C$_2$H$_5$ (leuprorelin) or a salt thereof (especially acetate) is preferred.

The abbreviations used herein are defined as follows:
Abbreviation Name
 N(4H$_2$-furoyl)Gly: N-tetrahydrofuroylglycine residue
 NAc: N-acetyl group
 D2Nal: D-3-(2-naphthyl)alanine residue
 D4ClPhe: D-3-(4-chlorophenyl)alanine residue
 D3Pal: D-3-(3-pyridyl)alanine residue
 NMeTyr: N-methyltyrosine residue
 Aph(Atz): N-[5'-(3'-amino-1'H-1',2',4'-triazolyl)]phenylalanine residue
 NMeAph(Atz): N-methyl-[5'-(3'-amino-1'H -1',2',4'-triazolyl)]phenylalanine residue
 DLys(Nic): D-(ε-N-nicotinoyl)lysine residue
 Dcit: D-citrulline residue
 DLys(AzaglyNic): D-(azaglycylnicotinoyl)lysine residue
 DLys(AzaglyFur): D-(azaglycylfuranyl)lysine residue
 DhArg(Et$_2$): D-(N,N'-diethyl)homoarginine residue
 DAph(Atz): D-N-[5'-(3'-amino-1'H-1',2',4'-triazolyl)]phenylalanine residue
 DhCi: D-homocitrulline residue
 Lys(Nisp): (ε-N-isopropyl)lysine residue
 hArg(Et$_2$): (N,N'-diethyl)homoarginine residue
 DSer(tBu): D-(O-t-butyl)serine residue
 DHis(ImBzl): D-(π-benzyl)histidine residue The abbreviations for amino acids are based on abbreviations specified by the IUPAC-IUB Commission on Biochemical Nomenclature [European Journal of Biochemistry, Vol. 138, pp. 9-37 (1984)] or abbreviations in common use in relevant fields. When an optical isomer may be present in amino acid, it is of the L-configuration, unless otherwise stated.

Sustained-release base materials used in the above-described sustained-release preparation are preferably biodegradable polymers etc., exemplified by polymers and copolymers that have been synthesized from one or more kinds selected from α-hydroxycarboxylic acids (e.g., glycolic acid, lactic acid, hydroxybutyric acid), hydroxydicarboxylic acids (e.g., malic acid), hydroxytricarboxylic acids (e.g., citric acid) etc., and that have a free carboxyl group, or mixtures thereof; poly-α-cyanoacrylic acid esters; polyamino acids (e.g., poly-γ-benzyl-L-glutamic acid); and maleic anhydride copolymers (e.g., styrene-maleic acid copolymers).

Polymerization may be of the random, block or graft type. When the above-mentioned α-hydroxycarboxylic acids, hydroxydicarboxylic acids and hydroxytricarboxylic acids have an optical active center in their molecular structures, they may be of the D-, L- or DL-configuration. Of these, lactic acid-glycolic acid polymers, poly-α-cyanoacrylic acid esters etc. are preferred. Greater preference is given to lactic acid-glycolic acid polymers.

The biodegradable polymer is preferably biodegradable polymer or lactic acid-glycolic acid copolymer consisting of a mixture of (A) a copolymer of glycolic acid and a hydroxycarboxylic acid represented by the general formula:

wherein R represents an alkyl group having 2 to 8 carbon atoms, and (B) a polylactic acid.

With respect to general formula [II] above, the linear or branched alkyl group represented by R, which has 2 to 8 carbon atoms, is exemplified by ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl. Preferably, a linear or branched alkyl group having 2 to 5 carbon atoms is used. Such alkyl groups include, for example, ethyl, propyl, isopropyl, butyl and isobutyl. More preferably, R is ethyl.

The hydroxycarboxylic acid represented by general formula [II] is exemplified by 2-hydroxybutyric acid, 2-hydroxyvaleric acid, 2-hydroxy-3-methylbutyric acid, 2-hydroxycaproic acid, 2-hydroxyisocaproic acid and 2-hydroxycapric acid, with preference given to 2-hydroxybutyric acid, 2-hydroxyvaleric acid, 2-hydroxy-3-methylbutyric acid and 2-hydroxycaproic acid, with greater preference given to 2-hydroxybutyric acid. Although the hydroxycarboxylic acid may be of the D-, L- or D,L-configuration, it is preferable to use a mixture of the D- and L-configurations wherein the ratio of the D-/L-configuration (mol %) preferably falls within the range from about 75/25 to about 25/75, more preferably from about 60/40 to about 40/60, and still more preferably from about 55/45 to about 45/55.

With respect to the copolymer of glycolic acid and a hydroxycarboxylic acid represented by general formula [II] (hereinafter referred to as glycolic acid copolymer), copolymerization may be of the random, block or graft type. A random copolymer is preferred.

The hydroxycarboxylic acid represented by general formula [II] may be used singly or in a mixture of one or more kinds in a given ratio.

With respect to the content ratio of glycolic acid and the hydroxycarboxylic acid represented by general formula [II] in glycolic acid copolymer (A) above, it is preferable that glycolic acid account for about 10 to about 75 mol % and hydroxycarboxylic acid for the remaining portion. More preferably, glycolic acid accounts for about 20 to about 75 mol %, and still more preferably about 40 to about 70 mol %, and hydroxycarboxylic acid for the remaining portion. The weight-average molecular weight of the glycolic acid copolymer is normally about 2,000 to about 100,000, preferably about 3,000 to about 80,000, and more preferably about 5,000 to about 50,000. The degree of dispersion of the glycolic acid copolymer (weight-average molecular weight/number-average molecular weight) is preferably about 1.2 to about 4.0, more preferably about 1.5 to about 3.5.

Glycolic acid copolymer (A) above can be produced by a known production method such as that described in Japanese Patent Unexamined Publication No. 28521/1986.

Although the polylactic acid may be of the D- or L-configuration or a mixture thereof, it is preferable that the ratio of the D-/L-configuration (mol %) fall within the range from about 75/25 to about 20/80. The ratio of the D-/L-configuration (mol %) is more preferably about 60/40 to about 25/75, and still more preferably about 55/45 to about 25/75. The weight-average molecular weight of said polylactic acid is preferably about 1,500 to about 100,000, more preferably about 2,000 to about 80,000, and still more preferably about 3,000 to about 50,000 or about 10,000 to 60,000 (more preferably about 15,000 to about 50,000). Also, the degree of dispersion of the polylactic acid is preferably about 1.2 to about 4.0, more preferably about 1.5 to about 3.5.

For producing a polylactic acid, two methods are known: ring-opening polymerization of lactide, a dimer of lactic acid, and dehydration polymerization condensation of lactic acid.

Glycolic acid copolymer (A) and polylactic acid (B) in the preparation base material of the present invention are used in a mixture wherein the (A)/(B) ratio (% by weight) falls within the range from about 10/90 to about 90/10. The mixing ratio (% by weight) is preferably about 20/80 to about 80/20, and more preferably about 30/70 to about 70/30.

If either component (A) or (B) is in excess, the preparation obtained shows a drug release pattern no more than that obtained with the use of component (A) or (B) alone; no linear release pattern is expected in the last stage of drug release from the mixed base material. Although the decomposition/elimination rate of glycolic acid copolymer and polylactic acid varies widely, depending on molecular weight or composition, drug release duration can be extended by increasing the molecular weight of polylactic acid added or lowering the mixing ratio (A)/(B), since the decomposition/elimination rate of glycolic acid copolymer is usually higher than that of polylactic acid. Conversely, drug release duration can be shortened by decreasing the molecular weight of polylactic acid added or increasing the mixing ratio (A)/(B). Drug release duration can also be adjusted by altering the kind and content ratio of hydroxycarboxylic acid represented by general formula [II].

When the biodegradable polymer used is polylactic acid or a lactic acid-glycolic acid copolymer (hereinafter simply referred to as lactic acid-glycolic acid polymer), the lactic acid/glycolic acid content ratio (mol %) is preferably 100/0 to 40/60, more preferably 100/0 to 45/55, and still more preferably 100/0 to 50/50.

The weight-average molecular weight of the lactic acid-glycolic acid polymer is preferably 3,000 to 100,000, more preferably 5,000 to 80,000. The degree of dispersion (weight-average molecular weight/number-average molecular weight) is preferably about 1.3 to about 4.0, more preferably about 1.5 to about 3.5.

The decomposition/elimination rate of lactic acid-glycolic acid polymer varies widely, depending on composition or molecular weight. However, drug release duration can be extended by lowering the glycolic acid ratio or increasing the molecular weight, because decomposition/elimination is usually delayed as the glycolic acid ratio decreases. Conversely, drug release duration can be shortened by increasing the glycolic acid ratio or decreasing the molecular weight. To obtain a sustained-release preparation(solid) of the long acting type (e.g., 1-6 months, preferably 1-4 months), it is preferable to use a lactic acid-glycolic acid polymer whose content ratio and weight-average molecular weight fall in the above ranges. If choosing a lactic acid-glycolic acid polymer that decomposes more rapidly than that whose content ratio and weight-average molecular weight fall in the above ranges, initial burst is difficult to suppress; if choosing a lactic acid-glycolic acid polymer that decomposes more slowly than that whose content ratio and weight-average molecular weight fall in the above ranges, it is likely that no effective amount of drug is released during some period.

Weight-average molecular weight, number-average molecular weight and degree of dispersion, as defined herein, are polystyrene-based molecular weights and degree of dispersion determined by gel permeation chromatography (GPC) with nine polystyrenes as reference substances with weight-average molecular weights of 120,000, 52,000, 22,000, 9,200, 5,050, 2,950, 1,050, 580, and 162, respectively. Measurements are taken using a GPC column KF804Lx2 (produced by Showa Denko) and an RI monitor L-3300 (produced by Hitachi, Ltd.), with chloroform as a mobile phase. Also, number-average molecular weight is calculated by dissolving the biodegradable polymer in an acetone-methanol mixed solvent, and titrating this solution with an alcoholic solution of potassium hydroxide with phenolphthalein as an indicator, to determine the terminal carboxyl group content. This molecular weight is hereinafter referred to as number-average molecular weight based on terminal group quantitation.

While the number-average molecular weight based on terminal group quantitation is an absolute value, that based on GPC measurement is a relative value that varies depending on various analytical conditions (e.g., kind of mobile phase, kind of column, reference substance, slice width, baseline); it is therefore difficult to have an absolute numerical representation of both values. In the case of polymers having a free carboxyl group at one end, that have been synthesized from lactic acid and glycolic acid by the catalyst-free dehydration polymerization condensation method, however, the number-average molecular weights based on GPC measurement and terminal group quantitation almost agree with each other. This fact means that the number-average molecular weight based on terminal group quantitation falls within the range from about 0.5 to about 2 times, preferably from about 0.7 to about 1.5 times, that based on GPC measurement.

A lactic acid-glycolic acid polymer can be produced by, for example catalyst-free dehydration polymerization condensation from a lactic acid and a glycolic acid, or ring-opening polymerization from a lactide and a cyclic compound such as glycolide by means of a catalyst (Encyclopedic Handbook of Biomaterials and Bioengineering Part A: Materials, Volume 2, Marcel Dekker, Inc., 1995).

Although the polymer synthesized by ring-opening polymerization is a polymer not having a carboxyl group, it is also possible to use a polymer prepared by chemically treating said polymer to render its terminal a free carboxyl group [Journal of Controlled Release, Vol. 41, pp. 249-257 (1996)].

The above-described lactic acid-glycolic acid polymer having a free carboxyl group at one end can be produced without any problems by known production methods (e.g., catalyst-free dehydration polymerization condensation method, see Japanese Patent Unexamined Publication No. 28521/1986); a polymer having a free carboxyl group elsewhere (not limited to terminals) can be produced by known production methods (e.g., see Patent Publication for WO94/15587).

Also, the lactic acid-glycolic acid polymer prepared by chemical treatment after ring-opening polymerization to render its terminal a free carboxyl group may be a commercial product of Boehringer Ingelheim KG, for example.

The sustained-release preparation suspension used for the production method of the present invention is a suspension prepared by adding anticoagulants mentioned below. In case of MC, the sustained-release preparation suspension is usually prepared about 1 mg to about 300 mg/ml, preferably, about 5 mg to about 1000 mg/ml for MC.

The sustained-release preparation suspension used for the production method of the present invention is a suspension prepared by adding an anticoagulant, e.g., a water-soluble saccharide [e.g., mannitol, lactose, glucose, starches (e.g., corn starch)], amino sugars (e/g/. glycine, alanine), protein (e.g., gelatin, fibrin, collagen), inorganic salt (e.g., sodium chloride, sodium bromide, potassium carbonate), or the like. Of these anticoagulants, mannitols, such as D-mannitol, are preferred.

Solvents for the suspension include, for example, water for injection (e.g., water produced by distillation, ultrafiltration etc.), UF water, RO water, ion exchange water, volatile solvents (e.g., ethanol, acetone), polyethylene glycol, vegetable oils, mineral oils, or mixtures thereof, with preference given to water for injection etc.

Also, surfactants, thickening agents, pH regulators etc. can be added as suspension stabilizers. Useful surfactants include, for example, polysorbates (e.g., polysorbate 80, polysorbate 20), Pluronics (e.g., Pluronic F68 (nonproprietary name polyoxyethylene [160] polyoxypropylene [30] glycol etc.), and polyoxyethylene hardened castor oils (e.g., polyoxyethylene hardened castor oil 50, polyoxyethylene hardened castor oil 60). Useful thickening agents include, for example, carboxymethyl celluloses (e.g., CMC-K, CMC-Na) and polyvinylpyrrolidone (PVP). Useful pH regulators include, for example, hydrochloric acid, sodium hydroxide, acetic acid, lactic acid, ammonium hydroxide, sodium carbonate, and sodium hydrogen carbonate.

The freeze-drying container for the production method of the present invention may be any container, as long as it is in common use for freeze-drying of sustained-release preparations such as MCs; for example, freeze-drying trays etc. are used. Said container is made of a metal (preferably stainless steel (SUS316, 304 etc.), glass, or porcelain. Further, the freeze-drying container for the production method of the present invention may be a plate form.

The size of said freeze-drying container may be chosen as appropriate according to freeze-drying scale. Specifically, freeze-drying containers ① about 5 mm to about 10,000 mm in width, about 5 mm to about 10,000 mm in length, and about 0.1 mm to about 500 mm in depth, preferably ② about 5 mm to about 7,000 mm in width, about 5 mm to about 7,000 mm in length, and about 1 mm to about 100 mm in depth, and more preferably ③ about 5 mm to about 500 mm in width, about 5 mm to about 300 mm in length, and about 5 mm to about 100 mm in depth, for example, are used. Although the width/length/depth ratio is not subject to limitation, it is normally about 1 to about 20 in width and about 1 to about 10 in length, preferably about 1 to about 10 in width and about 1 to about 6 in length, per 1 in depth.

The container capacity is, for example, about 10 ml to about 100,000 ml, preferably about 100 ml to about 5,000 ml, and more preferably about 3,000 ml.

Said freeze-drying container is partially hollowed for aspiration during freeze-drying, and normally has no ceiling plate.

The water-repelling base material used to cover said freeze-drying container is exemplified by ethylene fluoride resins (e.g., ethylene tetrafluoride resin, ethylene trifluoride resin, ethylene difluoride resin), vinylidene fluoride resin, propylene hexafluoride-ethylene tetrafluoride copolymer resin, modified fluorine resin, ethylene tetrafluoride resin-perfluoroalkoxyethylene copolymer resin, and ethylene tetrafluoride resin-ethylene copolymer resin, with preference given to ethylene fluoride resins (e.g., ethylene tetrafluoride resin, ethylene trifluoride resin, ethylene difluoride resin), specifically Teflon (trade name).

The freeze-drying container can be coated with a water-repelling base material by commonly known methods or methods based thereon, specifically plating, vapor deposition etc.

The solid sustained-release preparation obtained by the production method of this invention, includes any sustained-release preparations obtainable by the production method of this invention (i.e. freeze-drying method). The solid sustained-release preparation obtained by the production method of this invention includes a sustained-release preparation powder (e.g. MC powder), and also includes sustained-release preparations manufactured in various forms by known methods (e.g. pellet form, needle form, etc.).

The production method of the present invention is hereinafter described in more detail.

(1) Production method for a solid sustained-release preparation, characterized in that a sustained-release preparation (a sustained-release preparation suspension) is freeze-dried in a freeze-drying container whose inner face is partially or totally coated with an ice layer The water used to prepare an ice layer is exemplified by water for injection (e.g., distilled water) and ion exchange water.

The portion covered with an ice layer is a portion of, or the entire, inner face of the freeze-drying container; for example, it may be the bottom face alone, the entire bottom and side faces, a portion of the bottom face alone, or a portion of the bottom and side faces alone. The outer face of the container may also be coated with a water-repelling base material.

The thickness of the ice layer in the freeze-drying container may be chosen as appropriate according to the size of the container used, sustained-release preparation (sustained-release preparation suspension) volume, freeze-drying temperature, and other factors; for example, the thickness is normally about $1/1,000$ to about $4/5$, preferably about $1/500$ to about $1/5$, more preferably about $1/100$ to about $1/10$, and still more preferably about $1/10$, of the depth of the container, with preference given to thicknesses of not less than about 0.01 mm. More specifically, the thickness is normally about 0.01 mm to about 400 mm, preferably about 0.01 mm to about 200 mm, more preferably about 0.01 mm to about 30 mm, still more preferably about 0.1 mm to about 30 mm, yet still more preferably about 0.1 mm to about 10 mm, and most preferably about 1 mm.

An ice layer is prepared by dispensing water into the tray, and normally freezing it at about $-80°$ C. to about $0°$ C., preferably about $-50°$ C. to about $0°$ C.

After the ice layer is formed in the freeze-drying container, a sustained-release preparation (a sustained-release preparation suspension) is dispensed into the container and frozen to form a frozen layer of the sustained-release preparation (sustained-release preparation suspension).

In the case of microcapsules, the sustained-release preparation (sustained-release preparation suspension) is normally prepared to about 1 mg to about 300 mg/ml, preferably about 5 mg to about 1,000 mg/ml for microcapsule.

The volume of the sustained-release preparation (sustained-release preparation suspension) in the freeze-drying container may be chosen as appropriate according to the size of the container used, freeze-drying temperature, and other factors; for example, the thickness of the frozen layer of the sustained-release preparation (sustained-release preparation suspension) is normally about $1/1,000$ to about $4/5$, preferably about $1/500$ to about $1/5$, more preferably about $1/100$ to about $1/10$, and still more preferably about $1/10$, of the depth of the container. The volume of the sustained-release preparation (sustained-release preparation suspension) may also be about 0.1 ml to about 99.9 ml, preferably about 1 ml to about 90 ml, and more preferably about 1 ml to about 40 ml, per 100 ml container capacity. When the ice layer is about 1 mm from the bottom of the container, the frozen layer of the sustained-release preparation (sustained-release preparation suspension) may be about 1 to 10 times, preferably about 1 to 5 times, as thick as the ice layer.

For example, when the container used is about 5 mm to about 7,000 mm in width, about 5 mm to about 7,000 mm in length, and about 1 mm to 100 mm in depth, the ice layer thickness is normally about 0.01 mm to about 30 mm, preferably about 0.1 mm to about 30 mm, more preferably about 0.1 mm to 10 mm, and still more preferably about 1 mm. On the other hand, the frozen layer of the sustained-release preparation (sustained-release preparation suspension) is, for example, about 1 mm to about 20 mm, preferably about 2 mm to about 10 mm, and more preferably about 4 mm, from the bottom face ice layer.

The frozen layer of the sustained-release preparation (sustained-release preparation suspension) is prepared by dispensing a sustained-release preparation (a sustained-release preparation suspension), previously cooled to about −10° C. to about 20° C., preferably about 0° C. to 5° C., onto the ice layer, then normally freezing it at about −80° C. to about 0° C., preferably about −50° C. to about 0° C.

Two layers, i.e., an ice layer and a frozen layer of the sustained-release preparation (sustained-release preparation suspension), are thus prepared in the freeze-drying container.

Freeze-drying can be achieved by commonly known methods; for example, it can be achieved as directed in the above-mentioned patent publications that disclose microcapsules or microspheres.

Preferably, the freeze-drying can be achieved, for example, by completing the sublimation of frozen water in the freeze-drying container under reduced condition that the temperature in the freeze-drying container is 0° C. or below (preferably, −40° C. to 0° C., more preferably, −20° C. to 0° C., further preferably, −10° C. to 0° C.). More concretely, the freeze-drying can be achieved, by completing the sublimation of frozen water in the freeze-drying container under reduced condition that the temperature in the freeze-drying container (shelf temperature) is maintained 0° C. or below (preferably, −40° C. to 0° C., more preferably, −20° C. to 0° C., further preferably, −10° C. to 0° C.).

The temperature of the freeze-drying container (shelf temperature), mentioned above means the temperature of the container holding the freeze-drying samples or the temperature of the shelf contacting with the container. The frozen water, mentioned above means frozen free-water.

When the freeze-drying container (shelf temperature) is maintained at 0° C. or below (preferably, −40° C. to 0° C., more preferably, −20° C. to 0° C., further preferably, −10° C. to 0° C.), the temperature is maintained for more than about 0.1 hours, preferably for about 1 hour to about 500 hours, more preferably for about 5 hours to about 100 hours in order to complete the sublimation of frozen water in the freeze-drying container.

Under the freeze-drying method, mentioned above, the frozen water is sublimated at the temperature of 0° C. or below, that is, the temperature below the eutectic crystal or melting point, and the temperature in which the ice does not melt and the freeze-drying method provides the prevention of the collapsing of the freeze-drying cake, the prevention of the scattering of the MC powders around the outside of the freeze-drying container, high yield of the MC powders and obtaining the high quality of the MC powders.

(2) Production method for a solid sustained-release preparation, characterized in that a sustained-release preparation (a sustained-release preparation suspension) is freeze-dried in a freeze-drying container whose inner face is partially or totally coated with a water-repelling base material The portion covered with a water-repelling base material is a portion of, or the entire, inner face of the freeze-drying container; for example, it may be the bottom face alone, the entire bottom and side faces, a portion of the bottom face alone, or a portion of the bottom and side faces alone. The outer face of the container may also be coated with a water-repelling base material.

A sustained-release preparation (a sustained-release preparation suspension) is dispensed to a container and frozen to form a frozen layer of the sustained-release preparation (sustained-release preparation suspension).

In the case of microcapsules, the sustained-release preparation (sustained-release preparation suspension) is normally prepared to about 1 mg to about 300 mg/ml, preferably about 1 mg to about 300 mg/ml for microcapsule.

The volume of the sustained-release preparation (sustained-release preparation suspension) in the freeze-drying container may be chosen as appropriate according to the size of the container used, freeze-drying temperature, and other factors; for example, the thickness of the frozen layer of the sustained-release preparation (sustained-release preparation suspension) is normally about $1/1,000$ to about $4/5$, preferably about $1/500$ to about $1/5$, more preferably about $1/100$ to about $1/10$, and still more preferably about $1/10$, of the depth of the container. The volume of the sustained-release preparation (sustained-release preparation suspension) may also be about 0.1 ml to about 99.9 ml, preferably about 1 ml to about 90 ml, and more preferably about 1 ml to about 40 ml, per 100 ml container capacity. When the ice layer is about 1 mm from the bottom of the container, the frozen layer of the sustained-release preparation (sustained-release preparation suspension) may be about 1 to 10 times, preferably about 1 to 5 times, as thick as the ice layer.

For example, when the container used is about 5 mm to about 7,000 mm in width, about 5 mm to about 7,000 mm in length, and about 1 mm to 100 mm in depth, the ice layer thickness is normally about 0.01 mm to about 30 mm, preferably about 0.1 mm to about 30 mm, more preferably about 0.1 mm to 10 mm, and still more preferably about 1 mm. On the other hand, the frozen layer of the sustained-release preparation (sustained-release preparation suspension) is, for example, about 1 mm to about 20 mm, preferably about 2 mm to about 10 mm, and more preferably about 4 mm, from the bottom face ice layer.

The frozen layer of the sustained-release preparation (sustained-release preparation suspension) is prepared by dispensing a sustained-release preparation (a sustained-release preparation suspension), which is previously cooled to about −10° C. to about 20° C., preferably about 0° C. to 5° C., onto the ice layer, then normally freezing it about −80° C. to about 0° C., preferably about −50° C. to about 0° C.

A frozen layer of the sustained-release preparation (sustained-release preparation suspension) is thus prepared in the freeze-drying container.

Freeze-drying can be achieved in the same manner as in production method (1) above.

(3) Production method for a solid sustained-release preparation, characterized in that a sustained-release preparation (a sustained-release preparation suspension) is freeze-dried in a freeze-drying container whose inner face is coated with a water-repelling base material and partially or totally coated with an ice layer This method can be conducted in the same manner as production method (1) except that the freeze-drying container for production method (1) is replaced with a freeze-drying container whose inner face is coated with a water-repelling base material.

In this method, it is desirable that at least the entire portion of the inner face of the freeze-drying container, that comes in contact with the sustained-release preparation (sustained-release preparation suspension), be coated with a water-repelling base material.

The production method of the present invention has the advantages shown below.

(1) Because MC powders do not adhere to the tray, there is no need for MC powders removal using a scraper at time of their recovery.

(2) Because of obviation of the necessity of the MC powder removal using a scraper, environmental exposure time at time of MC powders recovery is shortened, thus reducing the risk of invasion of microorganisms etc. Also, because of the short environmental exposure time, the risk is reduced from the viewpoint of physicochemical stability, since MCs need water content control.

(3) Because of obviation of the necessity of MC powder's removal using a scraper, there is no risk of production and introduction of foreign substances due to friction between the tray and scraper.

(4) Because of minimum adhesion of MC powders and the tray, the MC powder recovery rate is high.

(5) Moreover, by using the freeze-drying method, mentioned above, MC powders are recovered more consistently and in higher yield.

Where necessary, freeze-drying of a sustained-release preparation (a sustained-release preparation suspension) by the production method of the present invention may be followed by heating under reduced pressure without causing mutual adhesion of sustained-release preparation particles, to remove the water and organic solvent from the sustained-release preparation. In this case, it is preferable that the suspension be heated at a temperature slightly higher than the intermediate glass transition point of the biodegradable polymer, as determined using a differential scanning calorimeter when the temperature is increased at a rate of about 10 to about 20° C. per minute. More preferably, the suspension is heated within the temperature range from the intermediate glass transition point of the biodegradable polymer to a temperature higher by about 30° C. than the glass transition point.

When a lactic acid-glycolic acid polymer is used as the biodegradable polymer, in particular, it is preferable that the suspension be heated within the temperature range from the intermediate glass transition point to a temperature higher by 20° C. than the glass transition point, more preferably within the temperature range from the intermediate glass transition point to a temperature higher by 10° C. than the glass transition point.

Although it varies depending on the amount of sustained-release preparation and other factors, heating time is preferably about 12 hours to about 168 hours, more preferably about 48 hours to about 120 hours, and still more preferably about 48 hours to about 96 hours, after the sustained-release preparation reaches a given temperature.

Any heating method can be used, as long as sustained-release preparation aggregates are uniformly heated.

Useful thermal drying methods include, for example, the method in which thermal drying is conducted in a constant-temperature chamber, fluidized bed chamber, mobile chamber or kiln, and the method using microwaves for thermal drying. Of these methods, the method in which thermal drying is conducted in a constant-temperature chamber is preferred.

The freeze-dried sustained-release preparation(solid) specimen thus obtained can be administered orally or non-orally as such or in the form of various dosage forms prepared using it as a starting material: Specifically, it can be administered as intramuscular, subcutaneous, visceral and other injectable preparations or implant preparations, nasal, rectal, uterine and other transdermal preparations, oral preparations [e.g., solid preparations such as capsules (e.g., hard capsules, soft capsules), granules and powders; liquids such as syrups, emulsions and suspensions] etc.

For example, the sustained-release preparation(solid) of the present invention can be prepared as injectable preparations by suspending in water with a dispersing agent (e.g., surfactants such as Tween 80 and HCO-60, polysaccharides such as sodium hyaluronate, carboxymethyl cellulose and sodium alginate), a preservative (e.g., methyl paraben, propyl paraben), an isotonizing agent (e.g., sodium chloride, mannitol, sorbitol, glucose, proline) etc. to yield an aqueous suspension, or by dispersing in a vegetable oil such as sesame oil or corn oil to yield an oily suspension, whereby a practically useful sustained-release injectable preparation(solid) is obtained.

When the sustained-release preparation(solid) of the present invention is used in the form of an injectable suspension, its particle diameter is chosen over such a range that the requirements concerning the degree of dispersion and needle passage are met. For example, the mean particle diameter normally ranges from about 0.1 to 300 μm, preferably from about 1 to 150 μm, and more preferably from about 2 to 100 μm.

The sustained-release preparation(solid) of the present invention can be prepared as a sterile preparation by such methods as the method in which the entire production process is aseptic, the method using gamma rays for sterilization, and the method in which a preservative is added, which methods are not to be construed as limitative.

Because of low toxicity, the above-described sustained-release preparation(solid) can be used safely in humans or non-human mammals (e.g., monkeys, bovines, swines, dogs, cats, mice, rats, rabbits).

Although varying widely depending on kind, content and dosage form of the active ingredient biologically active peptide, and duration of release of the biologically active peptide, target disease, subject animal species, method of administration and other factors, the dose of the sustained-release preparation(solid) may be set at any level, as long as the biologically active peptide is effective. The dose of the active ingredient biologically active peptide per administration can be preferably chosen as appropriate over the range from about 0.001 mg to 100 mg/kg body weight, more preferably from about 0.005 mg to 50 mg/kg body weight, and still more preferably from about 0.01 mg to 10 mg/kg body weight, per adult (50 kg body weight assumed) in the case of a 1-month release preparation(solid).

More specifically, when an LH-RH antagonist represented by general formula [Ia] or an LH-RH agonist represented by general formula [Ib], as described above, is used as the biologically active peptide, the sustained-release preparation (solid) of the present invention can be used as therapeutic/prophylactic agents for hormone-dependent diseases, including prostatic cancer, prostatic hypertrophy, endometriosis, hysteromyoma, metrofibroma, precocious puberty, breast cancer, gallbladder cancer, uterine cervical cancer, chronic lymphatic leukemia, chronic myelocytic leukemia; colorectal cancer, gastritis, Hodgkin's disease, malignant melanoma, metastatic/multiple myeloma, non-Hodgkin's lymphoma, non-small cell lung cancer, ovarian cancer, digestive ulcer, systemic fungal infection, small cell lung cancer, cardiac valvular disease, mastopathy, polycystic ovary, infertility, chronic anovulation, induction of appropriate ovulation in women, acnes, amenorrhea (e.g., secondary amenorrhea), cystic diseases of ovary and breast (including polycystic ovary), gynecologic cancers, ovarian hyperandrogenemia and hypertrichosis, AIDS due to T cell production mediated via thymus blastogenesis, and male sterilization for treatment of male sexual crime offenders, as drugs for contraception and mitigation of symptoms in premenstrual syndrome (PMS), as agents for in vitro fertilization (IVF), etc., and in particular, as therapeutic/prophylactic agents for prostatic cancer, prostatic hypertrophy, endometriosis, hysteromyoma, metrofibroma, precocious puberty etc., and as contraceptives.

Although varying widely depending on the dosage form of the biologically active peptide, desired duration of drug release, target disease, subject animal species, and other factors, the dose of said biologically active peptide may be set at any level, as long as the drug is effective. The dose of the drug per administration can be preferably chosen as appropriate over the range from about 0.001 mg to about 10 mg/kg body weight, more preferably from about 0.005 mg to about 5 mg/kg body weight, per adult in the case of a 1-month sustained-release preparation(solid) for cancer.

The dose of the sustained-release preparation(solid) per administration can be preferably chosen as appropriate over the range from about 0.005 mg to 50 mg/kg body weight, more preferably from about 0.01 mg to 30 mg/kg body weight per adult. The frequency of administration can be chosen as appropriate, depending on kind, content and dosage form of the active ingredient biologically active peptide, duration of release of the biologically active peptide, target disease, subject animal species and other factors, e.g., once every several weeks, one every month or once every several months.

BEST MODE FOR CARRYING OUT THE PRESENT INVENTION

The present invention is hereinafter described in more detail by means of the following working examples and reference examples, which are not to be construed as limitative, and which may be modified, as long as the scope of the present invention is not deviated from.

EXAMPLES

Reference Example 1

Preparation of Sustained-Release MC (1-Month Preparation) Suspension 2.4 g of gelatin and 15.2 g of leuprorelin acetate were dissolved in 15.0 g of distilled water under warming. To this solution, 321 g of a separately prepared dichloromethane solution of a lactic acid-glycolic acid copolymer (hereinafter referred to as PLGA) [lactic acid/glycolic acid=75/25 (mol %), weight-average molecular weight 10,500] (121 g of PLGA contained) was added, followed by emulsification with stirring using a mini-mixer for 2 minutes (rotation rate 10,000 rpm). This emulsion was added to 25 l of a previously prepared 0.1% aqueous solution of polyvinyl alcohol (PVA), followed by emulsification again. While this W/O/W emulsion was gently stirred, the solvent was removed over a period of about 3 hours. The MCs obtained were passed through a 75 μm sieve to remove coarse particles, then centrifuged. The MCs separated were washed with distilled water to remove the free drug and PVA, after which they were subjected to wet sieving through sieves of 250 μm and 90 μm pore size in the presence of a small amount of distilled water. 18.4 g of D-mannitol was added to the product suspension and dissolved to yield a MC suspension. The amounts of individual starting materials may be adjusted according to production scale.

Reference Example 2

Preparation of Sustained-Release MC (3-Month Preparation) Suspension 10.8 g of leuprorelin acetate was dissolved in 12.5 g of distilled water under warming. To this solution, 256 g of a separately prepared dichloromethane solution of a lactic acid polymer (hereinafter referred to as PLA) [weight-average molecular weight 16,000] (96 g of PLA contained) was added, followed by emulsification during stirring using a mini-mixer for 2 minutes (rotation rate 10,000 rpm). This emulsion was added to 25 l of a previously prepared 0.1% aqueous solution of polyvinyl alcohol (PVA), followed by emulsification again. While this W/O/W emulsion was gently stirred, the solvent was removed over a period of about 3 hours. The MCs obtained were passed through a 75 μm sieve to remove coarse particles, then centrifuged. The MCs separated were washed with distilled water to remove the free drug and PVA, after which they were subjected to wet sieving through sieves of 250 μm and 90 μm pore size in the presence of a small amount of distilled water. 18.4 g of D-mannitol was added to the product suspension and dissolved to yield a MC suspension. The amounts of individual starting materials may be adjusted according to production scale.

Example 1

In a freeze-drying tray (width 200 mm, length 100 mm, depth 20 mm), an ice layer about 1 mm in thickness was formed with water for injection at −30° C. An ice layer was also formed on the inner wall of the tray (ice lining). 80 ml of the MC suspension as obtained in Reference Example 1 above, previously cooled to about 5° C., was added onto the freeze-drying tray with the ice layer, and thoroughly frozen at about −30° C., followed by freeze-drying by a conventional method.

Separately, 80 ml of said MC suspension was added onto a freeze-drying tray without an ice layer, and thoroughly frozen at about −30° C., followed by freeze-drying by a conventional method.

After freeze-drying, each tray was inverted, and the status of detaching/recovery of the freeze-dried specimen therefrom was observed.

When the freeze-drying tray with an ice layer was used, the freeze-dried specimen was easily recovered from the tray, with no MC powder adhesion on the tray surface. On the other hand, when the freeze-drying tray without an ice layer was used, the freeze-dried specimen was not detached from the tray, with MC powder adhesion on the tray even after powder recovery using a scraper.

Example 2

80 ml of the MC suspension as obtained in Reference Example 1 above, previously cooled to about 5° C., was added to a freeze-drying tray (width 200 mm, length 100 mm, depth 20 mm), previously coated with Teflon (trade name), a water-repelling polymer, and thoroughly frozen at about −30° C., followed by freeze-drying by a conventional method.

Separately, 80 ml of said MC suspension was added to a freeze-drying tray without surface water-repelling treatment, and thoroughly frozen at about −30° C., followed by freeze-drying by a conventional method.

After freeze-drying, each tray was inverted, and the status of detaching/recovery of the freeze-dried specimen therefrom was observed.

When the freeze-drying tray with surface water-repelling treatment was used, the freeze-dried specimen was easily recovered from the tray, with no MC powder adhesion on the tray surface. On the other hand, when the freeze-drying tray without surface water-repelling treatment was used, the freeze-dried specimen was not detached from the tray, with MC powder adhesion on the tray even after powder recovery using a scraper.

Example 3

In the same Teflon-coated freeze-drying tray (width 200 mm, length 100 mm, depth 20 mm) as in Example 2, an ice layer about 1 mm in thickness was formed with water for injection at −30° C. An ice layer was also formed on the inner wall of the tray (ice lining). 80 ml of the MC suspension as obtained in Reference Example 1 above, previously cooled to about 5° C., was added to the tray and thoroughly frozen at about −30° C., followed by freeze-drying by a conventional method.

Separately, 80 ml of said MC suspension was added onto a freeze-drying tray without an ice layer and without surface water-repelling treatment, and thoroughly frozen at about −30° C., followed by freeze-drying by a conventional method.

After freeze-drying, each tray was inverted, and the status of detaching/recovery of the freeze-dried specimen therefrom was observed.

When the freeze-drying tray with surface water-repelling treatment and with an ice layer was used, the freeze-dried specimen was easily recovered from the tray, with no MC powder adhesion on the tray surface. On the other hand, when the freeze-drying tray without an ice layer and without surface water-repelling treatment was used, the freeze-dried specimen was not detached from the tray, with MC powder adhesion on the tray even after powder recovery using a scraper.

Example 4

Even when the freeze-drying tray size and ice layer thicknesses shown in Table 1 were combined variously, results similar to those in Examples 1 through 3 were obtained.

TABLE 1

| | Tray | | | Ice Layer | |
|---|---|---|---|---|---|
| | Length (mm) | Width (mm) | Depth (mm) | Bottom face (mm) | Side face (mm) |
| 1 | 8 | 8 | 2 | 0.1 | 0.03 |
| 2 | 8 | 8 | 10 | 0.4 | 0.1 |
| 3 | 8 | 30 | 2 | 0.2 | 0.1 |
| 4 | 8 | 30 | 10 | 0.4 | 0.1 |
| 5 | 30 | 8 | 5 | 0.4 | 0.1 |
| 6 | 30 | 8 | 20 | 1 | 0.2 |
| 7 | 30 | 30 | 5 | 0.4 | 0.1 |
| 8 | 30 | 30 | 20 | 1 | 0.2 |
| 9 | 450 | 30 | 5 | 0.4 | 0.1 |
| 10 | 450 | 30 | 20 | 1 | 0.2 |
| 11 | 450 | 30 | 60 | 2 | 0.5 |
| 12 | 450 | 270 | 45 | 2 | 0.5 |
| 13 | 450 | 270 | 20 | 1 | 0.2 |
| 14 | 450 | 270 | 60 | 3 | 1 |
| 15 | 450 | 2000 | 20 | 2 | 0.5 |
| 16 | 450 | 2000 | 45 | 1 | 0.2 |
| 17 | 450 | 2000 | 60 | 3 | 1 |
| 18 | 2000 | 2000 | 60 | 3 | 1 |
| 19 | 2000 | 2000 | 100 | 10 | 10 |
| 20 | 2000 | 7000 | 60 | 3 | 1 |
| 21 | 2000 | 7000 | 100 | 10 | 10 |
| 22 | 7000 | 2000 | 60 | 3 | 1 |
| 23 | 7000 | 2000 | 100 | 10 | 10 |
| 24 | 7000 | 7000 | 60 | 3 | 1 |
| 25 | 7000 | 7000 | 100 | 30 | 30 |

Example 5

15.1 g of leuprorelin acetate was dissolved in 15.0 g of distilled water under warming. To this solution, 323.6 g of a separately prepared dichloromethane solution of a lactic acid-glycolic acid copolymer (hereinafter referred to as PLGA) [lactic acid/glycolic acid=75/25 (mol %), weight-average molecular weight 10,500] (121 g of PLGA contained) was added, followed by emulsification with stirring using a mini-mixer for 2 minutes (rotation rate 10,000 rpm; temperature of the mixture: 40° C. or below). This emulsion was cooled to 18° C. to 19° C. and added to 25 l of a previously prepared 0.1% aqueous solution of polyvinyl alcohol (PVA) (18° C. to 19° C.), followed by emulsification again. While this W/O/W emulsion was gently stirred, the solvent was removed over a period of about 3 hours. The MCs obtained were passed through a 75 μm sieve to remove coarse particles, after which they were subjected to wet sieving through sieves of 90 μm pore size in the presence of a small amount of distilled water. 18.4 g of D-mannitol was added to the product suspension and dissolved to yield a MC suspension.

In a freeze-drying tray (width 170 mm, length 260 mm, depth 40 mm), an ice layer about 2 mm in thickness is formed with water for injection at −30° C. 400 ml of a MC suspension as mentioned above is added onto the freeze-drying tray with the ice layer, and thoroughly frozen at about −30° C., followed by freeze-drying by a conventional method or a method described in the following Example 7.

The freeze-dried specimen obtained by this method, is easily recovered from the tray, with no MC powder adhesion on the tray surface.

Example 6

15.1 g of leuprorelin acetate was dissolved in 13.0 g of distilled water under warming. To this solution, 323.6 g of a separately prepared dichloromethane solution of a lactic acid-glycolic acid copolymer (hereinafter referred to as PLGA) [lactic acid/glycolic acid=75/25 (mol %), weight-average molecular weight 10,500] (121 g of PLGA contained) was added, followed by emulsification with stirring using a mini-mixer for 2 minutes (rotation rate 10,000 rpm; temperature of the mixture: 40° C. or below). This emulsion was cooled to 18° C. to 19° C. and added to 25 l of a previously prepared 0.1% aqueous solution of polyvinyl alcohol (PVA) (18° C. to 19° C.), followed by emulsification again. While this W/O/W emulsion was gently stirred, the solvent was removed over a period of about 3 hours. The MCs obtained were passed through a 75 µm sieve to remove coarse particles, after which they were subjected to wet sieving through sieves of 90 µm pore size in the presence of a small amount of distilled water. 18.4 g of D-mannitol was added to the product suspension and dissolved to yield a MC suspension.

In a freeze-drying tray (width 170 mm, length 260 mm, depth 40 mm), an ice layer about 2 mm in thickness is formed with water for injection at −30° C. 400 ml of the MC suspension as mentioned above is added onto the freeze-drying tray with the ice layer, and thoroughly frozen at about −30° C., followed by freeze-drying by a conventional method described in Example 7.

The freeze-dried specimen obtained by this method, is easily recovered from the tray, with no MC powder adhesion on the tray surface.

Example 7

Application to Sustained-Release MC (1-Month Preparation) Suspension

In a freeze-drying tray (width 170 mm, length 260 mm, depth 40 mm), an ice layer about 2 mm in thickness was formed with water for injection at −30° C. An ice layer was also formed on the inner wall of the tray (ice lining). 200 mL of the MC suspension as obtained in Reference Example 1 above, previously cooled to about 5° C., was added onto the freeze-drying tray with ice layer, and thoroughly frozen at about −30° C., followed by freeze-drying by a following method.

After the MC suspension was frozen, the temperatures of the shelves in the freeze-drying apparatus was raised up to −5° C. at a rate of 20° C./hr, then the temperatures were kept around −5° C. for about 20 hours. After the ice was sublimated, the temperatures of the shelves were raised up to 51° C. at a rate of 20° C/hr, then kept the temperatures around 51° C. for about 48 hours.

After freeze drying, the appearance of the freeze-dried cake of MCs and the status of detaching/recovery of the freeze-dried cake of MCs therefrom were observed.

Crumbling of the cake of the freeze-dried MCs, and also dispersing and scattering of the MCs out of the tray were not observed. The cake of the freeze-dried MCs is easily recovered from the tray, with no MC powder adhesion on the tray.

Example 8

Application to Sustained-Release MC (3-Month Preparation) Suspension

In a freeze-drying tray (width 170 mm, length 260 mm, depth 40 mm), an ice layer about 2 mm in thickness is formed with water for injection at −30° C. An ice layer is also formed on the inner wall of the tray (ice lining). 200 mL of the MC suspension as obtained in Reference Example 2 above, previously cooled to about 5° C., is added onto the freeze-drying tray with ice layer, and thoroughly frozen at about −30° C., follows by freeze-drying by a following method.

After the MC suspension is frozen, the temperatures of the shelves in the freeze-drying apparatus are raised up to −5° C. at a rate of 20° C./hr, then the temperatures were kept around −5° C. for about 20 hours. After the ice is sublimated, the temperatures of the shelves are raised up to 51° C. at a rate of 20° C./hr, then the temperatures are kept around 51° C. for about 48 hours.

Crumbling of the cake of the freeze-dried MCs, and also dispersing and scattering of the MCs out of the tray are not observed. The cake of the freeze-dried MCs is easily recovered from the tray, with no MC powder adhesion on the tray.

Industrial Applicability

According to the production method of the present invention, the recovery rate of solid sustained-release preparations is markedly improved, because there is no adhesion of the freeze-drying container and solid sustained-release preparation so that the solid sustained-release preparation can be recovered without scraping. Furthermore, because of the short environmental exposure time, sterility retention for the solid sustained-release preparation is improved. In addition, by using the production method of the present invention which comprising completing the sublimation of frozen water in the freeze-drying container under a reduced condition that the temperatures in the freeze-drying container is 0° C. or below, the collapsing of the freeze-drying cake is prevented, the scattering of the MC powder is prevented and the freeze-dried MC powder can be recovered unexpectedly in a good form and high yield.

The invention claimed is:

1. A method for preventing scattering of a sustained-release microcapsule preparation in the production of a solid sustained-release microcapsule preparation, which comprises
   1) preparing the sustained-release microcapsule preparation by an aqueous drying method,
   2) dispensing water in a freeze-drying container and freezing it to form an ice layer,
   3) dispensing a water suspension of the sustained-release microcapsule preparation in the freeze-drying container to form a frozen layer, and
   4) freeze-drying the water suspension in the freeze-drying container comprising an inner face that is partially or wholly coated with an ice layer,
   so as to prevent scattering of the sustained-release microcapsule preparation,
   wherein said sustained-release microcapsule preparation contains a drug and a lactic acid-glycolic acid polymer, and
   wherein the water suspension comprises mannitol.

2. The method according to claim 1, wherein said ice layer has a thickness of 0.1 mm to 30 mm.

3. The method according to claim 1, wherein said inner face is further coated partially or wholly with a water-repelling base material which is ethylene tetrafluoride resin, ethylene trifluoride resin, ethylene difluoride resin, vinylidene fluoride resin, propylene hexafluoride-ethylene tetrafluoride copolymer resin, modified fluorine resin, ethylene tetrafluoride-perfluoroalkoxyethylene copolymer resin, or ethylene tetrafluoride-ethylene copolymer resin.

4. The method according to claim 1, wherein said drug is a biologically active peptide.

5. The method according to claim 4, wherein said biologically active peptide is leuprorelin or a salt thereof.

6. The method according to claim 1, wherein the content ratio of lactic acid and glycolic acid in said lactic acid-glycolic acid polymer is 100/0 to 40/60 (mol%).

7. The method according to claim 1, wherein said lactic acid-glycolic acid polymer has the weight-average molecular weight of 5,000 to 80,000.

8. The method according to claim 1, wherein said ice layer is prepared from distilled water.

9. The method according to claim 1, wherein said water suspension comprises the microcapsule preparation at about 1 mg/mL to about 300 mg/mL.

* * * * *